United States Patent
Wu

(10) Patent No.: US 11,432,586 B2
(45) Date of Patent: Sep. 6, 2022

(54) ELECTRONIC CIGARETTE

(71) Applicant: SHENZHEN SMOORE TECHNOLOGY LIMITED, Shenzhen (CN)

(72) Inventor: Zhenyu Wu, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 549 days.

(21) Appl. No.: 16/446,513

(22) Filed: Jun. 19, 2019

(65) Prior Publication Data
US 2020/0085101 A1 Mar. 19, 2020

(30) Foreign Application Priority Data

Sep. 19, 2018 (CN) .......................... 201821535047.8

(51) Int. Cl.
    *A24F 40/40* (2020.01)
    *A24F 40/10* (2020.01)
    (Continued)

(52) U.S. Cl.
    CPC .............. *A24F 40/40* (2020.01); *A24F 40/10* (2020.01); *A24F 40/42* (2020.01); *A61M 11/042* (2014.02); *A61M 15/06* (2013.01)

(58) Field of Classification Search
CPC .......... A24F 40/40; A24F 40/00; A24F 40/10; A24F 40/485; A61M 15/06
See application file for complete search history.

(56) References Cited

U.S. PATENT DOCUMENTS

2014/0053858 A1* 2/2014 Liu .......................... A24F 40/95
    131/329
2014/0196716 A1 7/2014 Liu
(Continued)

FOREIGN PATENT DOCUMENTS

CN     203168035 U     9/2013
CN     203182012 U     9/2013
(Continued)

OTHER PUBLICATIONS

CNIPA, Evaluation Report of Utility Model Patent No. ZL2018215250478, dated Aug. 11, 2019.
(Continued)

*Primary Examiner* — Alex B Efta
(74) *Attorney, Agent, or Firm* — Hemisphere Law, PLLC; Zhigang Ma

(57) ABSTRACT

An electronic cigarette comprises a power supply device, a screw sleeve and an atomizer. The power supply device is provided with a cavity accommodating the atomizer with a cigarette holder exposed outside. The atomizer is provided with a screw joint portion at one end thereof opposite to the cigarette holder, and a middle part of the screw joint portion is provided with a conduction head insulated from the screw sleeve that is made of a conductive material. A bottom part of the cavity is provided with an annular conductor, an adsorption element, and a pole needle extending through a middle part of the annular conductor, and the adsorption element is insulated from the pole needle. The screw sleeve can be adsorbed on the adsorption element, so that the screw sleeve is conductive with the annular conductor, and the conduction head is conductive with the pole needle.

18 Claims, 3 Drawing Sheets

(51) Int. Cl.
*A24F 40/42* (2020.01)
*A61M 11/04* (2006.01)
*A61M 15/06* (2006.01)

(56) References Cited

U.S. PATENT DOCUMENTS

| | | | | |
|---|---|---|---|---|
| 2014/0299140 | A1* | 10/2014 | Liu | A24F 40/40 131/329 |
| 2017/0164655 | A1* | 6/2017 | Chen | H05B 1/0244 |
| 2021/0378303 | A1* | 12/2021 | Liu | A24F 40/46 |

FOREIGN PATENT DOCUMENTS

| | | |
|---|---|---|
| CN | 103349363 A | 10/2013 |
| CN | 204444257 U | 7/2015 |
| CN | 204579887 U | 8/2015 |
| CN | 204907938 U | 12/2015 |
| CN | 205648929 U | 10/2016 |
| CN | 206273145 U | 6/2017 |
| CN | 206791644 U | 12/2017 |
| CN | 206808681 U | 12/2017 |
| WO | 2016101141 A1 | 6/2016 |
| WO | 2016101144 | 6/2016 |
| WO | 2018024004 A1 | 2/2018 |

OTHER PUBLICATIONS

CIPO (Canada), Requisition by the Examiner in Accordance With Subsection 86(2) of the Patent Rules for Canadian App. No. 3,044,000, dated Mar. 11, 2022, total 4 pages.

CNIPA, Evaluation Report of Utility Model Patent No. ZL2018215350478, dated Aug. 1, 2019, total 11 pages (including translation).

* cited by examiner

ELECTRONIC CIGARETTE

TECHNICAL FIELD

The utility model relates to a cigarette substitute, and specifically to an electronic cigarette.

BACKGROUND ART

With development of the electronic cigarette, the electronic cigarette products are also increasing in type and shape.

An existing electronic cigarette comprises a power supply device and an atomizer having a cigarette holder. The power supply device has a cavity for receiving a part of the atomizer in the cavity, and the cigarette holder is exposed out of the cavity, so as to facilitate use for the user.

However, since the atomizer having the cigarette holder is fixed to the power supply device, the user cannot adjust an angle of the cigarette holder when holding the smoking set. Moreover, the electronic cigarette using the existing connection mode can only be used after the user operates a rotating connection component for several times, which is complicated in operation and relatively high in manufacturing cost.

Therefore, it is quite necessary to provide a new electronic cigarette connection device to facilitate the use for the user.

SUMMARY OF THE UTILITY MODEL

The technical problem to be solved by the utility model is to provide an electronic cigarette.

The technical solution of the utility model adopted to solve the technical problem is to construct an electronic cigarette, comprising a power supply device, a screw sleeve and an atomizer;

The power supply device is provided with a cavity accommodating the atomizer with a cigarette holder exposed outside;

The atomizer is provided with a screw joint portion at one end thereof opposite to the cigarette holder, the screw sleeve is in screw joint with the screw joint portion, and a middle part of the screw joint portion is provided with a conduction head insulated from the screw sleeve that is made of an electrically conductive material;

A bottom part of the cavity is provided with an annular conductor, an adsorption element, and a pole needle extending through a middle part of the annular conductor, and the adsorption element is insulated from the pole needle;

The screw sleeve can be adsorbed on the adsorption element, so that the screw sleeve is conductive with the annular conductor, and the conduction head is conductive with the pole needle.

Preferably, the adsorption element is a magnet, the screw sleeve is made of a ferromagnetic material, and the screw sleeve is provided with an annular retainer ring corresponding to the adsorption element at one end thereof away from the cigarette holder.

Preferably, the screw sleeve is in screw joint and electrically conductive with the screw joint portion, and the conduction head is electrically insulated from the screw joint portion.

Preferably, the screw joint portion is made of a nonmagnetic material.

Preferably, the screw joint portion is made of copper or brass.

Preferably, the screw sleeve is provided with an internal thread which is in screw joint with the screw joint portion.

Preferably, the atomizer is rotatably arranged within the cavity.

Preferably, frictional force between the screw sleeve and the screw joint portion is larger than frictional force of mutual rotation between the screw sleeve and the power supply device.

Preferably, the adsorption element is annular, and is coaxially arranged with the annular conductor.

Preferably, the annular conductor is provided with a locating mechanism for clamping the adsorption element, and the locating mechanism includes one of a resilient arm, a locating detent, and a locating bulge, or a combination thereof.

Preferably, the annular conductor includes a first tube segment and a second tube segment, the first tube segment has an internal diameter larger than that of the second tube segment, and the adsorption element is arranged within the first tube segment;

the first tube segment is provided with a locating ring in an inner ring of one end thereof opposite to the second tube segment to secure the adsorption element, and the screw sleeve is inserted into the locating ring, and conductive with the locating ring and the annular conductor;

the pole needle is extended through a middle part of the adsorption element.

Implementing the electronic cigarette of the utility model has the following advantageous effects: the atomizer is adsorptively connected to the power supply device through the screw sleeve, which is fast and convenient. Meanwhile, the screw sleeve is processed by a ferromagnetic material, which is convenient in processing and low in cost.

BRIEF DESCRIPTION OF THE DRAWINGS

Hereinafter, the utility model is further described with reference to the accompanying drawings and embodiments. In the drawings.

DETAILED EMBODIMENT OF THE UTILITY MODEL

For a clearer understanding of the technical features, objects and effects of the utility model, specific embodiments of the utility model will now explicitly described with reference to the accompanying drawings.

Figure 1:
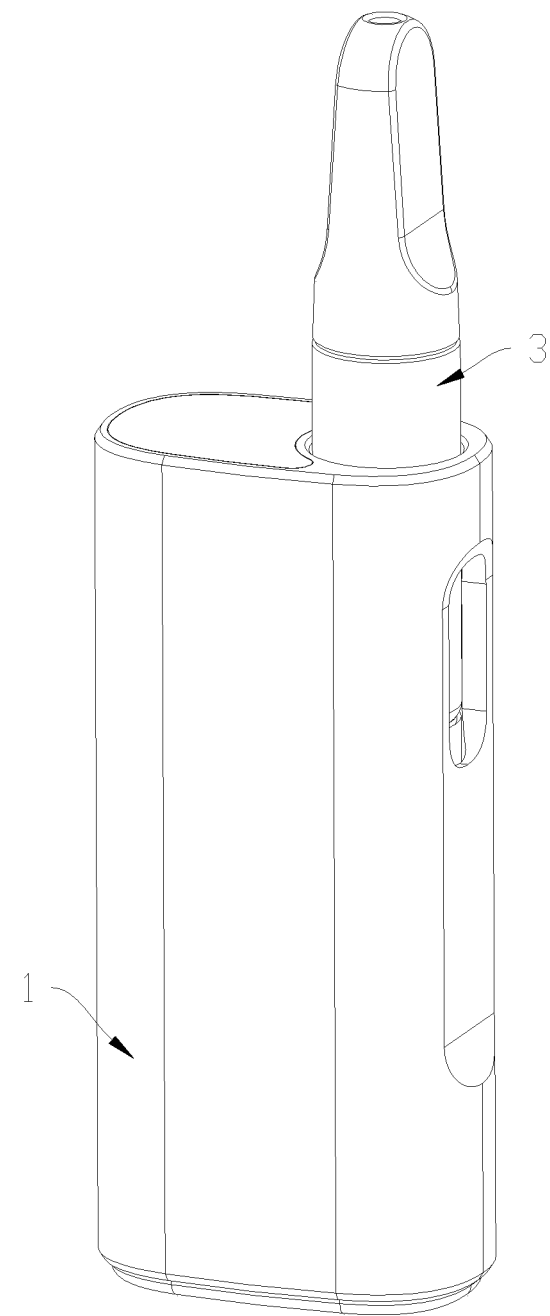
FIG. 1 is a structure diagram of an electronic cigarette in one embodiment of the utility model.
Figure 2:
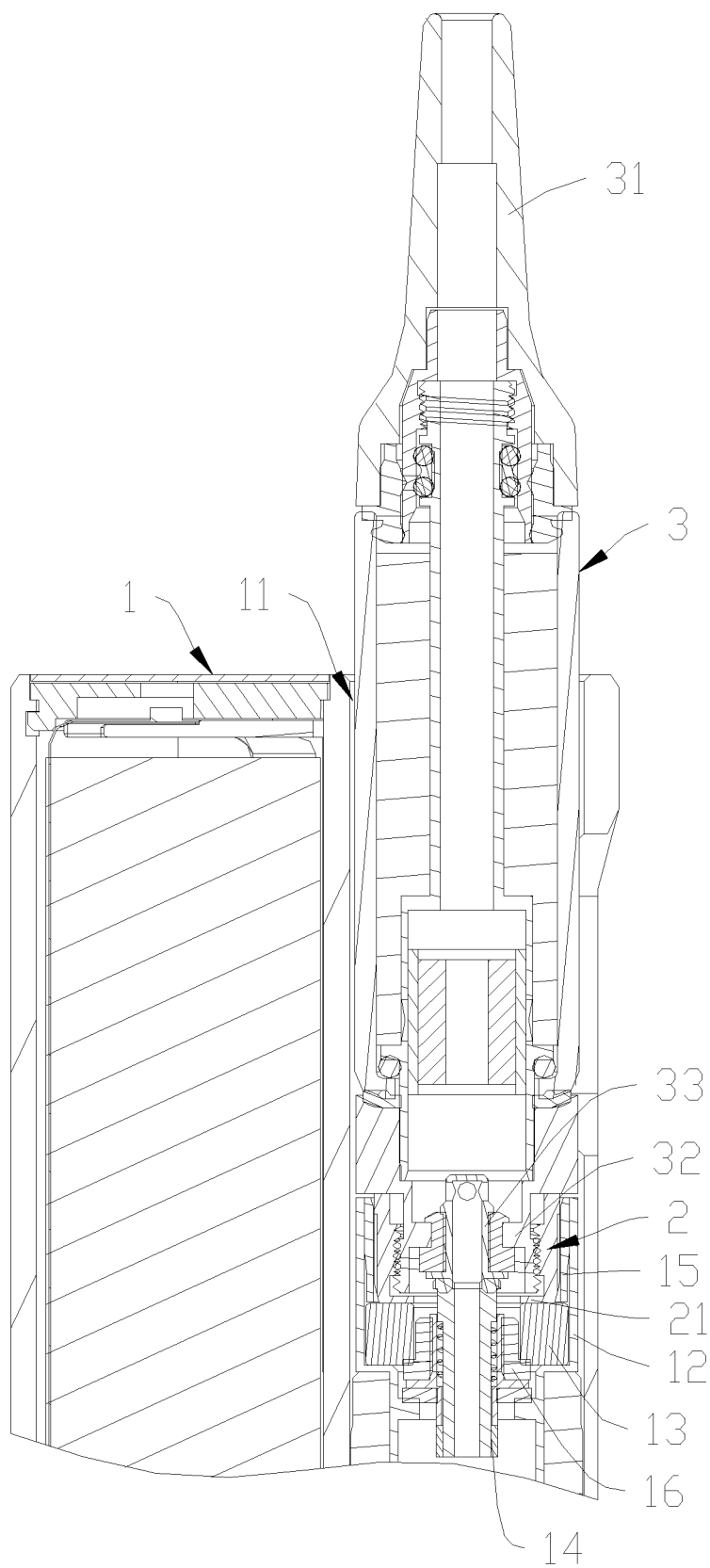
FIG. 2 is a profile structure diagram of the electronic cigarette in FIG. 1.
Figure 3:
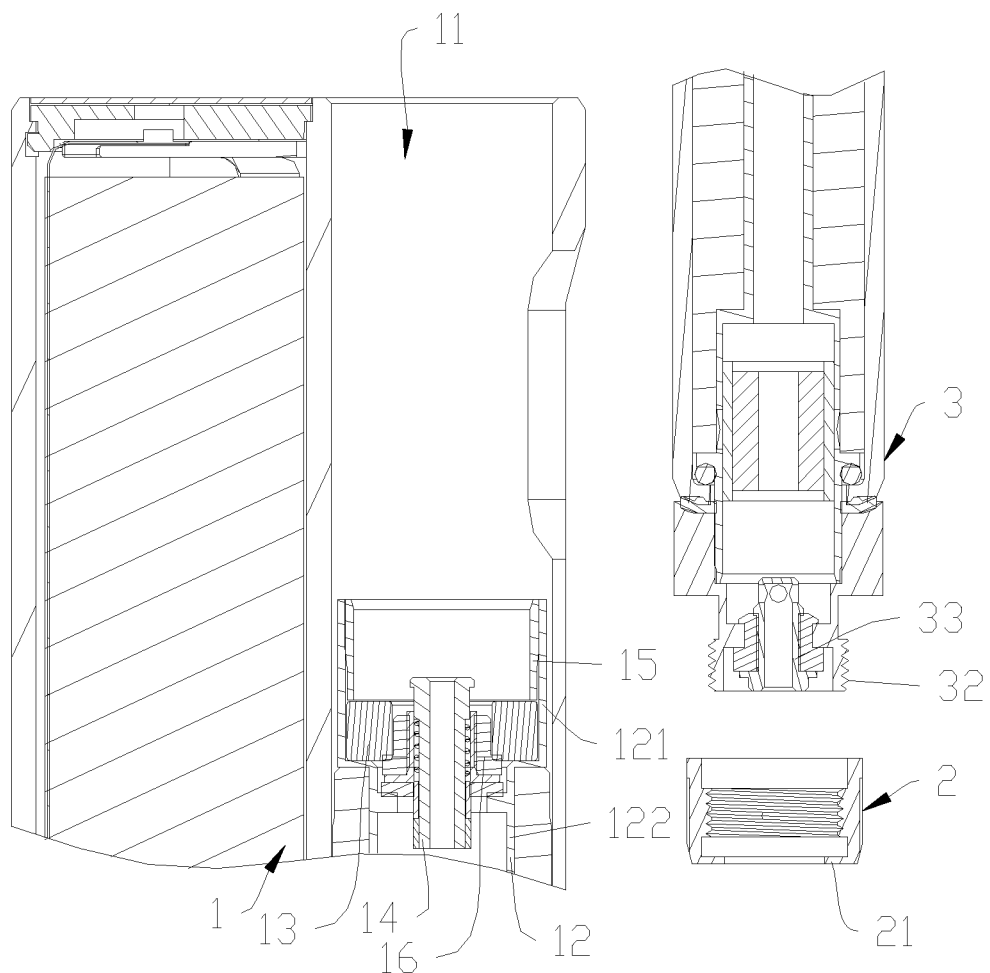
FIG. 3 is an exploded diagram of an atomizer, a screw sleeve and a power supply device of the electronic cigarette in FIG. 2.

As shown in FIGS. 1-3, an electronic cigarette in one preferred embodiment of the utility model comprises a power supply device 1, a screw sleeve 2 and an atomizer 3, wherein the power supply device 1 is provided with a cavity 11 accommodating the atomizer 3 with a cigarette holder 31 exposed outside to facilitate use for the user.

The atomizer 3 is provided with a screw joint portion 32 at one end thereof opposite to the cigarette holder 31, and the screw sleeve 2 is in screw joint with the screw joint portion 32. The screw sleeve 2 is tubular, and may be an internal thread or an external thread. In this embodiment, the screw sleeve 2 is provided with an internal thread which is in screw joint with the screw joint portion 32. A middle part of the screw joint portion 32 is provided with a conduction head 33 insulated from the screw sleeve 2 that is made of a conductive material, so that the screw sleeve 2 and the conduction head 33 can be respectively conductive with positive and negative electrodes of the power supply device 1.

Generally, the screw joint portion 32 is also made of a conductive material, the screw sleeve 2 is in screw joint and conductive with the screw joint portion 32, and the conduction head 33 is insulated from the screw joint portion 32. The screw joint portion 32 is made of a nonmagnetic material. For example, the screw joint portion 32 is made of copper or brass.

In other embodiments, the screw joint portion 32 also may be made of an insulating material, and after the screw sleeve 2 is in screw joint with the screw joint portion 32, one end of the screw sleeve 2 is conductive with an electrode on the atomizer 3.

A bottom part of the cavity 11 is provided with an annular conductor 12, an adsorption element 13, and a pole needle 14 extending through a middle part of the annular conductor 12, and the adsorption element 13 is insulated from the pole needle 14. The screw sleeve 2 can be adsorbed on the adsorption element 13, so that the screw sleeve 2 is conductive with the annular conductor 12, and the conduction head 33 is conductive with the pole needle 14.

Preferably, in order to increase adsorption force, the screw sleeve 2 is provided with an annular retainer ring 21 corresponding to the adsorption element 13 at one end thereof away from the cigarette holder, and the annular retainer ring 21 can increase an adsorption area with the adsorption element 13, thereby increasing the adsorption force. In other embodiments, the screw sleeve 2 can be further provided with one or more adsorption portions capable of increasing the adsorption area at one end thereof away from the cigarette holder, and the more adsorption portions are distributed circumferentially.

The atomizer 3 is adsorptively connected to the power supply device 1 through the screw sleeve 2, which is fast and convenient. Meanwhile, the screw sleeve 2 is processed by a ferromagnetic material, which is convenient in processing and is low in cost.

Preferably, the adsorption element 13 is a magnet, and the screw sleeve 2 is made of a ferromagnetic material, so they can be adsorbed mutually. Considering materials and processing costs, the screw sleeve 2 is preferably made of a free-cutting steel material.

Further, the atomizer 3 is rotatably arranged within the cavity 11. Since the screw sleeve 2 allows the atomizer 3 to be movably connected to the power supply device 1 without being directly connected, they can rotate mutually, so that a direction of the flat-shaped cigarette holder 31 on the atomizer 3 can be adjusted.

Preferably, frictional force between the screw sleeve 2 and the screw joint portion 32 is larger than frictional force of mutual rotation between the screw sleeve 2 and the power supply device 1, so as to prevent the screw sleeve 2 from falling from the screw joint portion 32 on the atomizer 3, so as to be adsorbed on the adsorption element 13 within the cavity 11.

Generally, the adsorption element 13 is annular, and is coaxially arranged with the annular conductor 12, which can ensure the atomizer 3 to be adsorbed with the adsorption element 13 when rotating.

In some embodiments, the annular conductor 12 includes a first tube segment 121 and a second tube segment 122, and the first tube segment 121 has an internal diameter larger than that of the second tube segment 122, so as to form a step inside the annular conductor 12. The adsorption element 13 is arranged within the first tube segment 121 to be axially located by the step inside the annular conductor 12.

The first tube segment 121 is provided with a locating ring 15 in an inner ring of one end thereof opposite to the second tube segment 122 to axially secure the adsorption element 13. Generally, the locating ring 15 is also a conductor, and the screw sleeve 2 is inserted into the locating ring 15, and electrically conductive with the locating ring 15 and the annular conductor 12. The locating ring 15 has an external diameter at one end thereof smaller than that of the other end thereof, which facilitates the smaller end to be inserted into the annular conductor 12. Preferably, the locating ring 15 is provided with a tapered slope at a middle part of an outer ring thereof so as to transit outer side faces of both ends thereof. In addition, the locating ring 15 is provided with a chamfering in an inner ring of one end thereof facing to an opening of the cavity 11 to facilitate insertion of the screw sleeve 2.

In other embodiments, the annular conductor 12 can be further provided with a locating mechanism for clamping the adsorption element 13, and the locating mechanism includes one of a resilient arm, a locating detent, and a locating bulge, or a combination thereof. The locating mechanism can be arranged on a side wall of the first tube segment 121, and can also be arranged on an end location of the first tube segment 121 to clamp and secure the adsorption element 13.

The pole needle 14 is extended through a middle part of the adsorption element 13. Preferably, an insulating sleeve 16 is sleeved between the adsorption element 13 and the pole needle 14, so that the power supply device 1 supplies power to the atomizer 3 via the annular conductor 12 and the pole needle 14 respectively.

It shall be understood that the above technical features can be used in any combination without limitation.

The above-mentioned are only embodiments of the utility model, not limitation on the extent of the utility model. Equivalent structures or equivalent flow alternations made by using the description and the accompanying drawings of the utility model, or direct or indirect application in other relevant technical fields shall be similarly included in the extent of protection of the utility model.

What is claimed is:

1. An electronic cigarette, comprising a power supply device (1), a screw sleeve (2) and an atomizer (3),
    wherein the power supply device (1) is provided with a cavity (11) accommodating the atomizer (3) with a cigarette holder (31) exposed outside the cavity (11);
    the atomizer (3) is provided with a screw joint portion (32) at one end thereof opposite to the cigarette holder (31), the screw sleeve (2) is in screw joint with the screw joint portion (32), and a middle part of the screw joint portion (32) is provided with a conduction head (33) insulated from the screw sleeve (2) that is made of an electrically conductive material;
    a bottom part of the cavity (11) is provided with an annular conductor (12), an adsorption element (13), and a pole needle (14) extending through a middle part of the annular conductor (12), and the adsorption element (13) is insulated from the pole needle (14);
    the screw sleeve (2) can be adsorbed on the adsorption element (13), so that the screw sleeve (2) is conductive with the annular conductor (12), and the conduction head (33) is conductive with the pole needle (14);
    the annular conductor (12) includes a first tube segment (121) and a second tube segment (122), wherein the first tube segment (121) has an internal diameter larger than that of the second tube segment (122), and the adsorption element (13) is arranged within the first tube segment (121);

the first tube segment (121) is provided with a locating ring (15) in an inner ring of one end thereof opposite to the second tube segment (122) to secure the adsorption element (13), and the screw sleeve (2) is inserted into the locating ring (15), and electrically conductive with the locating ring (15) and the annular conductor (12); and the pole needle (14) is extended through a middle part of the adsorption element (13).

2. The electronic cigarette according to claim 1, wherein the adsorption element (13) is a magnet, the screw sleeve (2) is made of a ferromagnetic material, and the screw sleeve (2) is provided with an annular retainer ring (21) corresponding to the adsorption element (13) at one end thereof away from the cigarette holder.

3. The electronic cigarette according to claim 1, wherein the screw sleeve (2) is in screw joint and electrically conductive with the screw joint portion (32), and the conduction head (33) is electrically insulated from the screw joint portion (32).

4. The electronic cigarette according to claim 3, wherein the screw joint portion (32) is made of a nonmagnetic material.

5. The electronic cigarette according to claim 4, wherein the screw joint portion (32) is made of copper or brass.

6. The electronic cigarette according to claim 1, wherein the screw sleeve (2) is provided with an internal thread which is in screw joint with the screw joint portion (32).

7. The electronic cigarette according to any one of claim 1, wherein the atomizer (3) is rotatably arranged within the cavity (11).

8. The electronic cigarette according to claim 7, wherein frictional force between the screw sleeve (2) and the screw joint portion (32) is larger than frictional force of mutual rotation between the screw sleeve (2) and the power supply device (1).

9. The electronic cigarette according to claim 7, wherein the adsorption element (13) is annular, and is coaxially arranged with the annular conductor (12).

10. An electronic cigarette, comprising a power supply device (1), a screw sleeve (2) and an atomizer (3) comprising a cigarette holder (31), wherein the power supply device (1) is provided with a cavity (11) accommodating the atomizer (3) with the cigarette holder (31) exposed outside the cavity (11);

the atomizer (3) is provided with a screw joint portion (32) at one end thereof opposite to the cigarette holder (31), the screw sleeve (2) is in screw joint with the screw joint portion (32), and a middle part of the screw joint portion (32) is provided with a conduction head (33) insulated from the screw sleeve (2) that is made of an electrically conductive material;

a bottom part of the cavity (11) is provided with an annular conductor (12), an adsorption element (13), and a pole needle (14) extending through a middle part of the annular conductor (12), and the adsorption element (13) is insulated from the pole needle (14);

the screw sleeve (2) can be adsorbed on the adsorption element (13), so that the screw sleeve (2) is electrically conductive with the annular conductor (12), and the conduction head (33) is electrically conductive with the pole needle (14);

the annular conductor (12) comprising two tube segments with different diameters (121, 122), and the adsorption element (13) is positioned in one of the two tube segments with a larger dimeter (121), and at a step formed between the two tube segments (121, 122), and a locating ring (15) inside the tube segment with the larger diameter secures the adsorption element (13); and the pole needle (14) is extended through a middle part of the adsorption element (13).

11. The electronic cigarette according to claim 10, wherein the adsorption element (13) is a magnet, the screw sleeve (2) is made of a ferromagnetic material, and the screw sleeve (2) is provided with an annular retainer ring (21) corresponding to the adsorption element (13) at one end thereof away from the cigarette holder.

12. The electronic cigarette according to claim 10, wherein the screw sleeve (2) is in screw joint and electrically conductive with the screw joint portion (32), and the conduction head (33) is electrically insulated from the screw joint portion (32).

13. The electronic cigarette according to claim 12, wherein the screw joint portion (32) is made of a nonmagnetic material.

14. The electronic cigarette according to claim 13, wherein the screw joint portion (32) is made of copper or brass.

15. The electronic cigarette according to claim 10, wherein the screw sleeve (2) is provided with an internal thread which is in screw joint with the screw joint portion (32).

16. The electronic cigarette according to any one of claim 10, wherein the atomizer (3) is rotatably arranged within the cavity (11).

17. The electronic cigarette according to claim 16, wherein frictional force between the screw sleeve (2) and the screw joint portion (32) is larger than frictional force of mutual rotation between the screw sleeve (2) and the power supply device (1).

18. The electronic cigarette according to claim 16, wherein the adsorption element (13) is annular, and is coaxially arranged with the annular conductor (12).

* * * * *